United States Patent [19]

Küpper et al.

[11] 4,016,220

[45] Apr. 5, 1977

[54] PROCESS FOR THE PREPARATION OF 9-TRICOSENE AND 9-HENEICOSENE

[75] Inventors: Friedrich-Wilhelm Küpper; Roland Streck, both of Marl, Germany

[73] Assignee: Chemische Werke Huels Aktiengesellschaft, Marl, Germany

[22] Filed: Feb. 12, 1976

[21] Appl. No.: 657,621

[30] Foreign Application Priority Data

Mar. 22, 1975 Germany ............................ 2512741

[52] U.S. Cl. ............................ 260/683 D; 252/464; 424/84
[51] Int. Cl.² .................... C07C 3/62; A01N 17/14
[58] Field of Search ................................ 760/683 D

[56] References Cited

UNITED STATES PATENTS

| | | | |
|---|---|---|---|
| 3,726,938 | 4/1973 | Berger | 260/683 D |
| 3,776,974 | 12/1973 | Gautier et al. | 260/683 D |
| 3,932,616 | 1/1976 | Mercsz et al. | 424/84 |

Primary Examiner—Delbert E. Gantz
Assistant Examiner—G. E. Schmitkons
Attorney, Agent, or Firm—Millen & White

[57] ABSTRACT

Higher alkenes with a double bond in the 9-position, e.g. 9-tricosene and/or 9-heneicosene, are economically prepared by a metathesis reaction of suitable alkene starting materials.

12 Claims, No Drawings large commercial scale, since they are all inherently based on stoichiometric reactions of natural substances or derivatives thereof with expensive auxiliarly chemicals and form economically worthless by-products.

PROCESS FOR THE PREPARATION OF 9-TRICOSENE AND 9-HENEICOSENE

BACKGROUND OF THE INVENTION

This invention relates to a process for the preparation of 9-tricosene and 9-heneicosene, the cis-isomers of which are essential components of the sex pheromone of the housefly *Musca domestica*.

As is known, pheromones are substances which serve in general to stimulate chemically mediated behavioral interactions of organisms with one another, in a narrower sense such interactions of insects with one another. Thus, among the pheromones are counted primarily sex attractants, as well as substances causing the expression of alarm, aggregation, attack, defense, etc., of the insects; these pheromones are generally effective even in minute quantities. By the use of refined analysis and synthesis methods, numerous pheromones have been isolated in recent years, explained with regard to their constitution and in part even synthesized. Among these pheromones is cis-9-tricosene, the sex attractant of the housefly, which is also known under the name of muscalure; see D. A. Carlson et al, Science 174:76–78 (1971). It has been discovered that, in addition to cis-9-tricosene, several other cis-olefins with a double bond in the 9-position are effective as sex pheromones; in particular, a mixture of cis-9-tricosene and cis-9-heneicosene in a weight ratio of 7:3 is said to possess optimum effectiveness, as has been reported by A. Mansingh et al, Can. Entomol. 104:1963–65 (1972).

The sex pheromones are of considerable practical interest inasmuch as it is possible with their aid to selectively combat individual, damaging types of insects. The procedure followed is to attract individual insects of the type to be combated with the aid of the sex pheromone and then to destroy the insects by means of insecticides or electric traps and/or to prevent the insects from reproducing by chemosterilization or radiosterilization. In this way, the populations of destructive types of insects can be reduced to a tolerable level without the danger of exerting an adverse effect on harmless or useful types of insects.

The common housefly *Musca domestica* is generally counted among the destructive insects, since it can transmit numerous diseases and deposits eggs in foodstuffs which are rendered unfit for consumption due to the evolving maggots.

The most effective component of the sex pheromone of the housefly, cis-9-tricosene, was isolated, characterized and synthesized for the first time by D. A. Carlson et al by means of a Wittig synthesis from 1-nonanal and 1-bromotetradecane; see Science 174: 76 – 78 (1971).

Further syntheses of cis-9-tricosene which have become known in the meantime are:

The alkylation of pentadecinyllithium with n-octyl bromide and the subsequent partial hydrogenation of 9-tricosine reported by K. Eiter in Naturwiss. (Natural Sciences) 59:468 (1972);

Reaction of erucic acid with 2 moles of methyllithium and subsequent Huang-Minlon reduction of the ketone by R. L. Cargill and M. G. Rosenblum, J. Org. Chem. 57:3971 (1972);

Reaction of oleic acid with 2 moles of n-pentyllithium and/or of oleonitrile and n-pentylmagnesium bromide and subsequent Huang-Minlon reduction reported by T. L. Ho and C. M. Wong in Can. J. Chem. 52:1923 (1974);

Combined electrolysis (crossed Kolbe synthesis) of the sodium salts of oleic acid and enanthic acid in a methanolic sodium methylate solution by G. W. Gribble et al, reported in Chem. Comm. 735 (1973); and The Wittig synthesis from 1-nonanal and tetradecyl bromide by H. J. Bestmann et al, "Chemiker-Ztg." (Chemists' Periodical) 98:161 (1974).

None of these multistage syntheses offers the possibility of producing the sex pheromone inexpensively on a large commercial scale, since they are all inherently based on stoichiometric reactions of natural substances or derivatives thereof with expensive auxiliarly chemicals and form economically worthless by-products.

OBJECTS OF THE INVENTION

Accordingly, it is a general object of this invention to provide a process for the production of 9-tricosene and/or 9-heneicosene which minimizes or eliminates the aforementioned problems facing the current state of the art.

Another object of this invention is to provide a simple and economical method for the direct preparation of cis-9-tricosene and/or cis-9-heneicosene.

A further object of this invention is to provide a process for preparing cis-9-alkene pheromones in good yield from readily available alkene starting materials.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing a process for preparing a compound selected from the group consisting of 9-tricosene, 9-heneicosene and mixtures thereof, which comprises metathetically reacting:

a. an alkene of at least 10 carbon atoms having an n-nonylidene radical;

b. at least one member selected from the group consisting of an alkene of at least 13 carbon atoms having an n-dodecylidene radical and an alkene of at least 15 carbon atoms having an n-tetradecylidene radical; and c. a catalytic amount of an olefin metathesis catalyst substantially free of oligomerization and isomerization activity with respect to said reactants, said catalyst comprising a compound of a metal in Group VB to VIIB of the Periodic Table to form said 9-tricosene, 9-heneicosene or mixtures thereof.

DETAILED DISCUSSION

Suitable alkenes useful for this invention are those carrying the alkylidene residues required to produce 9-tricosene and 9-heneicosene with the aid of a metathesis catalyst. Preferably employed for this purpose are alkenes containing $C_9$- and $C_{14}$-alkylidene residues for the preparation of 9-tricosene and $C_9$- and $C_{12}$-alkylidene residues for the preparation of 9-heneicosene.

So long as the alkene starting materials contain at least one of the desired $C_9$-, $C_{12}$- or $C_{14}$-alkylidene residues, the total chain length is not critical. For example, both 1-decene (C 10) and 9-octadecene (C 18) contain the $C_9$-alkylidene residue, with 9-octadecene advantageously forming two $C_9$-alkylidene radicals upon cleavage of the ethylene bond. Similar compounds containing the $C_9$-alkylidene residue include 2-undecene, 3- dodecene, 4-tridecene, 5-tetradecene, 6-pentadecene, 7-hexadecene, 8-heptadecene, etc.

For the preparation of 9-heneicosene, 2-tetradecene is presently preferred while similar compounds containing the $C_{12}$-alkylidene residue include 1-tridecene, 3-pentadecene, 4-hexadecene, 5-heptadecene, 6-octadecene, 7-octadecene, etc.

For the preparation of 9-tricosene, 1-pentadecene and 2-hexadecene are presently preferred, although similar compounds containing the $C_{14}$-alkylidene residue can be used, e.g. 3-heptadecene, 4-octadecene, 5-nonadecene, 6-eicosene, 7-heneicosene, etc.

The starting materials can be linear (straight chain) or branched so long as the $C_9$-, $C_{12}$- and $C_{14}$-alkylidene residues are linear, but n-isomers are preferred.

These alkenes then react under the effect of the metathesis catalyst forming, inter alia, an isomeric mixture of the desired compounds 9-tricosene and 9-heneicosene, respectively.

Suitable alkene starting materials obtainable and/or producible in a simple manner include but are not limited to 1-decene, 9-octadecene, 2-hexadecene, 1-pentadecene and 2-tetradecene. Among these, 1-decene, 2-tetradecene, 2-hexadecene and 9-octadecene can readily be prepared as products and/or secondary products known in the prior art.

The production of α-olefins, e.g. from petroleum, is well known in the current state of the art. The most important processes in this connection worth mentioning are the thermal cracking of higher paraffins (F. Asinger, "Die Petrolchemische Industrie" (The Petrochemical Industry) Akademie Publishers, Berlin, 1971, pp. 306 et seq. and the oligomerization of ethylene by means of aluminum trialkyls (German Pat. Nos. 878,560 and 1,190,930) or titanium-containing (German Unexamined Laid-Open Application DOS 1,518,795) or nickel-containing (DOS 2,054,009) catalyst systems.

It is furthermore known that α-olefins are isomerized with a shift of the double bond, forming a complex mixture of olefins having a double bond which is generally not in the terminal position. These positional isomers are contained in equilibrium in comparable amounts. With the use of certain catalysts and brief reaction times, however, conditions can be established wherein the mixture contains high proportions of 2-olefins. Thus, DOS 2,209,379 describes the selective isomerization of 1-hexadecene to a mixture of 88% of 2-hexadecene and 8% of 3-hexadecene wherein there is merely 4% of unreacted starting material, with the use of a molecular sieve coated with metallic sodium (the sieve being of calcium alumosilicate) as the catalyst and a reaction time of 10 minutes at 25° C.

9-Octadecene can be readily produced, for example, from 2 moles of 1-decene, with ethylene being split off, on disproportionation catalysts (DOS 1,618,466).

As is known, metathesis catalysts are catalysts which, on the one hand, are capable of the already mentioned disproportionation under exchange of alkylidene residues and, on the other hand, are capable of triggering the ring-opening polymerization of cycloolefins with the formation of polyalkenamers. These catalysts include homogeneous and heterogeneous catalysts containing compounds of metals of Subgroups V to VII of the Periodic Table, predominantly compounds of niobium, tantalum, molybdenum, tungsten and rhenium, as well as optionally compounds of the metals of Main Groups I to III of the Periodic Table, e.g. the alkyls or hydrides thereof, optionally with further ligands, e.g. halogen, alkoxyl or carboxylate or, in place thereof, Lewis acids. The metathesis catalysts, as is known, can further contain activating additives, e.g. alcohols, epoxides, tert.-butyl hypochlorite, peroxides, carboxylic acids, aromatic nitro compounds, vinyl halides, vinyl and allyl ethers, vinyl and allyl esters, etc. See German Published Application DAS 1,072,811; French Pat. Nos. 1,394,380 and 1,467,720; Dutch Patent Applications 65–10331, 66–05105, 66–14413, 67–04424, 67–14559, 68–06208, 68–06211 and 68–06209.

The process of this invention can be conducted with homogeneous as well as heterogeneous catalysts.

Two conditions, however, should always be met by the catalysts employed herein:

1. They should have no isomerizing activity, or a minimum of such activity (less than 3%); and 2. They should not convert the olefins used into oligomers or polymers, or should do so only to a limited extent (less than 1%).

Suitable such homogeneous catalysts include but are not limited to the conventional catalysts set out below:

$WCl_6$/EtOH/EtAlCl$_2$ (DOS 1,618,466);
$WCl_6$/dichloroisopropanol/ethyl aluminum sesquichloride (G. Dall'Asta et al, Chim. Ind. Milan 55(2):142–146 (1973);
$[Bu_4N]^+$ $[Mo(CO)_5Cl]^-$/MeAlCl$_2$ (DOS 2,047,270);
$Mo(CO)_6$/$[Bu_4N]^+Cl^-$/methyl aluminum sesquichloride (DOS 2,062,448);
$(P\phi_3)_2MoCl_2(NO)_2$/methyl aluminum sesquichloride (U.S. Pat. No. 3,558,518);
$[NR_4]^+[_{W(CO)_5}COR']^-$/MeAlCl$_2$ (U.S. Pat. No. 3,689,433).

Preferably, a homogeneous catalyst is employed comprising tungsten hexachloride, ethanol and ethyl aluminum dichloride, in a preferred molar ratio of the individual components of 1:1–3:4–5, especially of 1: 3: 5.

The heterogeneous metathesis catalysts used in accordance with this invention comprise (a) a support material and (b) at least one oxide of one or more elements of Group VIIB or VIIB of the Periodic Table of the elements.

Suitable support materials are well known in the art and include but are not limited to those commercially available aluminum oxides or oxides of the elements of Group IV of the Periodic Table of the elements which are solid under the contemplate reaction conditions, preferably silicon dioxides. These difficult-to-melt oxides ordinarily contain a minor proportion, e.g. 0.01–1.5%, preferably 0.1–1.0%, of alkali metal ions stemming from the manufacturing process, e.g. in the case of aluminum oxide, about 0.4% by weight of $Na_2O$ is suitable.

Preferably, oxides of molybdenum and rhenium are used as the catalyst component (b); rhenium heptoxide is particularly preferred.

The heterogeneous catalysts can be prepared conventionally, e.g. by simply mixing the components together. However, a preferred process resides in impregnating the support material with the solution of a suitable oxide precursor compound of the above-mentioned transition metals and then activating the support. The term "activation" means a heat or other treatment whereby the compounds are converted into the corresponding oxides. Preferably, a catalyst is utilized in the present process wherein aluminum oxide is impregnated with a solution of a perrhenate, especially ammonium perrhenate, and then heated in an air or oxygen stream so that the perrhenate is converted into rhenium oxide. The conversion of the compounds of the aforementioned transition metals into the oxides is generally accomplished by simple heating in a temperature range of 300°–650° C., preferably in the range of 350°–450° C.

The heterogeneous metathesis catalysts usable in the process of this invention generally contain 1–30 parts, preferably 5–20 parts, of molybdenum oxide or rhenium oxide in the valence stage active during the metathesis reaction per 100 parts of support material.

In principle, all metathesis catalysts suitable for the ring-opening polymerization of cyclic olefins having at least one unsubstituted ring double bond and/or for the disproportionation of acyclic olefins are useful in the process of this invention, which include but are not limited to heterogeneous metathesis catalysts meeting one or more of the following criteria:

a. those in which component (a) is a particulate aluminum oxide or silicon dioxide;

b. those in which the metal of component (b) is an oxide of molybdenum or rhenium;

c. those in which component (b) is rhenium heptoxide;

d. those in which component (a) is an aluminum oxide containing 0.1–1.0% alkali metal as $Na_2O$;

e. those in which component (a) is particulate aluminum oxide having an average particle size mean diameter of 1–6 mm; a surface area of 250–350 $m^2m/g$; a pore volume of 0.45–0.55 $cm^3/g$; a bulk density of 700–900 g/l, and an alkali content of 0.02–1.0 wt.%;

f. those of (a) through (e) inclusive containing 1–30 parts, preferably 5–20 parts by weight of active metal oxide per 100 parts of support material.

The process of this invention can be effected discontinuously as well as continuously. Suitably, the course of the reaction is chosen so that the thus-formed 9-tricosene and/or 9-heneicosene is separated as soon as possible from the reaction zone. The product can then optionally be subjected to a distillation purification.

The reaction can optionally also be accomplished in an inert solvent, i.e. one which does not interfere with metathetical reactions employing the aforementioned catalysts. Suitable inert solvents are well known in the art and are generally characterized as aliphatic, alicyclic, aromatic and/or halogenated hydrocarbons. Suitable such solvents include but are not limited to aliphatic hydrocarbons, e.g. pentane, hexane, heptane, n- and iso-octane, isononane (hydrogenated propene trimer), n-decane, isododecane (hydrogenated propene tetramer); cycloaliphatic hydrocarbons, e.g. cyclopentane, cyclohexane and the substitution products thereof, e.g. methylcyclopentane, methylcyclohexane, ethylcyclohexane, isopropylcyclohexane, cyclooctane, decahydronaphthalene, etc.; hydrogenated terpenes, e.g. pinane and camphane; aromatic hydrocarbons, e.g. benzene, toluene, o-, m- p-xylene, ethylbenzene, o-, m-, p-diethylbenzene, n-propylbenzene, isopropylbenzene, other mono- to polyalkyl benzenes, tetrahydronaphthalene, etc.; and halogenated derivatives of the above, e.g. methylene chloride, chloroform, carbon tetrachloride, 1,2-dichloroethylene, trichloroethylene, tetrachloroethylene, chlorobenzene, o-dichlorobenzene, trichlorobenzene (mixture of isomers), bromobenzene, fluorobenzene, 1,2-dichloroethane, etc. Preferably, solvents are employed which cannot participate as reactants in a Friedel-Crafts reaction with olefins present, i.e. the starting material or the desired product, so as to avoid Friedel-Crafts side reactions.

It is essential that the inert solvents as well as the alkene starting materials be made maximally free of water and other proton donors, as well as of compounds having electron donor functions (Lewis bases), by means of a suitable known purification technique. Except for very small quantities which are optionally used for obtaining special effects, such impurities generally impair the catalyst activity.

The process of the present invention is generally conducted at temperatures of about 0° C. The reaction temperature has an upper limit determined by an increase in undesired side reactions as well as by the thermal stability of the catalyst and its support, and a lower limit determined by an excessive reduction of the reaction velocity. The process is advantageously carried out at temperatures of between 40° and 180° C., especially between 50° and 120° C., with heterogeneous catalysts and at temperatures of between 0° and 60° C., especially between 10° and 40° C., with homogeneous catalysts. Given stability of a support material, reaction temperatures will be chosen so that isomerization side reactions are extensively prohibited. Reaction times required as those typical of metathesis reactions and vary from several seconds to several days, generally 0.25–10 hours at the preferred temperatures.

The process of this invention can be conducted discontinuously as well as continuously. Suitably, the process is conducted so that the 9-tricosene and/or the 9-heneicosene are removed as quickly as possible from the reaction zone and the starting materials are maintained in contact with the catalyst until they are entirely consumed.

The olefin mixtures prepared according to this invention can be worked up by means of generally customary methods, e.g. vacuum distillation or crystallization. If necessary, it is possible to add methods for fine purification, such as zone melting or a cis-trans-isomer separation, e.g. by fractional desorption from silver zeolites according to DOS 2,140,706. However, it is known that extreme configurative purity of 9-tricosene and 9-heneicosene is unneccessary for obtaining an attractant effect, since the trans-isomers merely have a far weaker activity and, above all, do not block the receptors, so that they can be considered as a not entirely inert pheromone diluent. Thus, an extreme enrichment of the most active pheromone components cis-9-tricosene and/or cis-9-heneicosene, generally contained in the thus-prepared olefin mixtures in concentrations up to 20–30%, is unneccessary, the less so inasmuch as they are used anyway in highly diluted form. The process of this invention is distinguished by great economy in this respect as well.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure of any way whatsoever. In the following Examples, the temperatures are set forth uncorrected in degrees Celsius; the data are indicated in percent by weight based on the olefin mixture present at the termination of the reaction.

EXAMPLE 1

Preparation of 9-tricosene with the aid of a homogeneous methathesis catalyst:

In a so-called Schlenk vessel, the olefins percolated over aluminum oxide, namely 9-octadecene and 2-hexdecene, in amounts of 20 ml. of 9-octadecene and 4.4 ml. of 2-hexadecene, were combined with a catalyst consisting of the following components: 0.1 millimole of $WCl_6$ (0.05-molar solution in benzene), 0.3 mmol ethanol (1-molar solution in cyclohexane), and 0.5 mmol ethyl aluminum dichloride (1-molar solution in cyclohexane). With a reaction temperature of 20° C., the tricosene contents listed in Table 1 below could be detected after the reaction times which are likewise set forth in the table.

TABLE 1

| Reaction Time (min.) | Tricosene Content (% by Weight) |
|---|---|
| 5 | 1.0 |
| 15 | 4.0 |
| 30 | 6.5 |
| 60 | 7.8 |
| 120 | 10.4 |

EXAMPLE 2

Analogously to the procedure described in Example 1, equal amounts of olefin mixture were reacted with the same quantity of catalyst, but at 50° C. In this process, 8.6% by weight of tricosene was obtained already after 5 minutes, and 11.8% by weight of tricosene after 15 minutes.

EXAMPLE 3

In the apparatus described in Example 1, and following the procedure of Example 1, 10 ml. of 9-octadecene and 8.8 ml. of 2-hexadecene were combined at 20° C. with the catalyst mentioned in Example 1 (0.1 mmol $WCl_6$, 0.3 mmol $C_2H_5OH$, 0.5 mmol $C_2H_5AlCl_2$). The results indicated in Table 2 below were thus obtained.

TABLE 2

| Reaction Time (min.) | Tricosene Content (% by Weight) |
|---|---|
| 5 | 3.8 |
| 15 | 4.5 |
| 30 | 9.1 |
| 60 | 10.8 |
| 120 | 15.5 |

EXAMPLE 4

Example 1 was repeated, except that 4.4 ml. of 1-pentadecene was used in place of 2-hexdecene. After 5 minutes, 2.9 by weight of tricosene was obtained, and after 30 minutes, 6.1% by weight of tricosene was produced.

EXAMPLE 5

Example 1 was repeated, with the difference that 20 ml. of 1-decene was utilized in place of 9-octadecene. Within 5 minutes, 4.8% by weight of tricosene was formed and within 30 minutes, 5.7% by weight of tricosene was obtained.

EXAMPLE 6

Preparation of 9-tricosene with the aid of heterogeneous metathesis catalysts:

A three-necked flask equipped with an internal thermometer and boiling capillary was charged with a mixture of 196 g. (0.79 mole) of 9-octadecene and 82 g. (0.36 mole) of 2-hexadecene under an inert gas (argon). The flask was provided with a circulation apparatus consisting of a riser pipe, a Liebig condenser, a Soxhlet-type, thermostat-controllable extractor, and a graduated dropping funnel disposed thereunder with pressure equalizing means and thermostat control. The extractor served for accommodating the heterogeneous metathesis catalyst, the dropping funnel was for the purpose of controlling the amount of alkene mixture passing through the catalyst, which mixture could return from the dropping funnel into the three-necked flask. By way of a vacuum nipple attached above the extractor, low boiling components were withdrawn and condensed in a cooling trap. The extractor contained 31.1 g. of a rod-shaped catalyst (diameter 4 mm.) containing molybdenum and having the following characteristics:

| | |
|---|---|
| Support: | aluminum oxide ($Al_2O_3$) |
| Molybdenum content: | 15.0% $MoO_3$ |
| Additional components: | 3.0% CoO; 0.025% $Na_2O$; 0.025% $Fe_2O_3$ |
| Surface: | 330 m²/g. |
| Bulk density: | 500 g./l. |
| Pore volume: | 0.83 cm³/g. |

At a reaction temperature of 60° C., 1.5 % by weight of tricosene could be detected after a reaction time of 6 hours and with a throughput of 200 ml. of olefin mixture per hour.

EXAMPLE 7

Following the procedure outlined in Example 6, 142 g. (0.56 mole) of 9-octadecene and 82 g. (0.37 mole) of 2-hexadecene were reacted at a reaction temperature of 100° C. After 5 hours and with a throughput of 200 ml. of olefin mixture per hour, 7.4% by weight of tricosene was obtained.

EXAMPLE 8

According to the process described in Example 6, 295 g. (1.18 moles) of 9-octadecene and 113 g. (0.5 mole) of 2-hexadecene were reacted at a reaction temperature of 60° C. on 39 g. of a rhenium-containing catalyst.

The catalyst was prepared as follows: 88 g. of an aluminum oxide (surface area: 300 m²/g., pore volume: 0.5 cm³/g., bulk density: 880 g./l.; alkali content: 0.4% by weight $Na_2O$) was impregnated with a solution of 11 g. of ammonium perrhenate in 100 ml. of distilled water; excess water was withdrawn from the forced-circulation evaporator, the remaining residue was dried under vacuum at 100°–120° C., and the product was then heated for 5–20 hours in a tubular furnace to 380°–420° C. After a reaction time of 5 hours and with a throughput of 200 ml. of olefin mixture per hour, 6.6% by weight of tricosene was obtained. In the tricosene separated by distillation, the proportion of cis-tricosene was 22%. According to the result of an ozonolysis, the double bond was in the 9-position to an extent of 89%.

EXAMPLE 9

Example 8 was repeated, except that, on the one hand, the reaction temperature was 100° C. and, on the other hand, 196 g. (0.79 mole) of 9-octadecene and 82 g. (0.36 mole) of 2-hexadecene were employed. After a reaction time of 5 hours and with a throughput of 200 ml. of olefin mixture per hour, the 9-tricosene content was 13% by weight. The cis-isomer contained in the pure alkene separated by distillation amounted to 26%.

EXAMPLE 10

A mixture of 9-triscosene and 9-heneicosene was prepared by following the process described in Example 8, namely by conducting, over 39 g. of the aforedescribed rehenium-containing catalyst, at 60° C., a mixture of 196 g. (0.79 mole) of 9-octadecene, 58 g. (0.26 mole) of 2-hexadecene, and 16 g. (0.08 mole) of 2-tetradecene. After a reaction time of 5 hours and with a throughput of 200 ml. of olefin mixture per hour, 3.2% by weight of tricosene and 1.4% by weight of heneicosene were obtained. The content of the cis-isomer was 24%.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a compound selected from the group consisting of 9-tricosene, 9-heneicosene and mixtures thereof, which comprises metathetically reacting:
   a. an alkene of at least 10 carbon atoms having an n-nonylidene radical;
   b. at least one member selected from the group consisting of an alkene of at least 13 carbon atoms having an n-dodecylidene radical and an alkene of at least 15 carbon atoms having a n-tetradecylidene radical; and
   c. a catalytic amount of an olefin metathesis catalyst substantially free of oligomerization and isomerization activity with respect to said reactants, said catalyst comprising a compound of a metal in Group VB to VIIB of the Periodic Table to form said 9-tricosene, 9-heneicosene or mixtures thereof.

2. A process according to claim 1, wherein said catalyst is a homogeneous metathesis catalyst and the reaction is effected at a temperature of 0°–60° C.

3. A process according to claim 2, wherein said metathesis catalyst comprises tungsten hexachloride, ethylaluminum dichloride and a catalyst activating amount of ethanol.

4. A process according to claim 1, wherein said catalyst is a heterogeneous methathesis catalyst deposited on a solid catalyst support material and the reaction is effected at a temperature of 40°–180° C.

5. A process according to claim 4, wherein said catalyst support is an alkali metal oxide-containing aluminum oxide and said catalyst is an oxide of molybdenum or rhenium.

6. A process according to claim 5, wherein said catalyst is rhenium heptoxide.

7. A process according to claim 1, wherein (a) is 1-decene or 9-octadecene and (b) is 2-hexadecene or 1-pentadecene, whereby 9-tricosene is formed.

8. A process according to claim 1, wherein (a) is 1-decene or 9-octadecene and (b) is 2-tetradecene, whereby 9-heneicosene is formed.

9. A process according to claim 1, wherein (a) is 1-decene or 9-octadecene and (b) is a mixture of 2-tetradecene with 2-hexadecene or 1-pentadecene, whereby a mixture of 9-tricosene and 9-heneicosene is formed.

10. A process according to claim 9, wherein said catalyst is a heterogeneous metathesis catalyst comprising an oxide of molybdenum or rhenium deposited on an alkali metal oxide-containing aluminum oxide support and said reaction is effected at a temperature of 50°–120° C.

11. A process according to claim 10, wherein said oxide is rhenium heptoxide.

12. A process according to claim 9, wherein said catalyst is a homogeneous metathesis catalyst comprising tungsten hexachloride, ethylaluminum dichloride and a catalyst activating amount of ethanol and said reaction is effected at a temperature of 10°–40° C.

* * * * *